(12) United States Patent
Kaffenberger et al.

(10) Patent No.: US 11,244,456 B2
(45) Date of Patent: Feb. 8, 2022

(54) SYSTEM AND METHOD FOR IMAGE SEGMENTATION AND DIGITAL ANALYSIS FOR CLINICAL TRIAL SCORING IN SKIN DISEASE

(71) Applicant: Ohio State Innovation Foundation, Columbus, OH (US)

(72) Inventors: Benjamin Kaffenberger, Columbus, OH (US); Metin Nafi Gurcan, Winston-Salem, NC (US)

(73) Assignee: Ohio State Innovation Foundation, Columbus, OH (US)

( * ) Notice: Subject to any disclaimer, the term of this patent is extended or adjusted under 35 U.S.C. 154(b) by 43 days.

(21) Appl. No.: 16/753,582

(22) PCT Filed: Oct. 3, 2018

(86) PCT No.: PCT/US2018/054054
§ 371 (c)(1),
(2) Date: Apr. 3, 2020

(87) PCT Pub. No.: WO2019/070775
PCT Pub. Date: Apr. 11, 2019

(65) Prior Publication Data
US 2020/0302608 A1 Sep. 24, 2020

Related U.S. Application Data

(60) Provisional application No. 62/567,395, filed on Oct. 3, 2017.

(51) Int. Cl.
*G06K 9/00* (2006.01)
*G06T 7/00* (2017.01)
(Continued)

(52) U.S. Cl.
CPC .......... *G06T 7/0016* (2013.01); *A61B 5/0077* (2013.01); *A61B 5/444* (2013.01);
(Continued)

(58) Field of Classification Search
CPC ...................... A61B 5/444; G06T 2207/30088
See application file for complete search history.

(56) References Cited

U.S. PATENT DOCUMENTS 6,567,682 B1  5/2003  Osterweil et al.
6,571,003 B1  5/2003  Hillebrand et al.
(Continued)

FOREIGN PATENT DOCUMENTS

WO    2017/093793 A1    6/2017

OTHER PUBLICATIONS

International Search Report and Written Opinion issued by the International Searching Authority (ISA/US) in PCT Application No. PCT/US2018/054054 dated Dec. 10, 2018. 11 pages.
(Continued)

*Primary Examiner* — Hadi Akhavannik
(74) *Attorney, Agent, or Firm* — Meunier Carlin & Curfman LLC

(57) ABSTRACT

Disclosed are systems and methods for clinical trial assessment of skin disease treatment. The disclosure includes obtaining a series of digital images over a period of time, wherein each digital image includes an affected area of the subject; identifying characteristic morphologies and lesions in the affected area of the subject in each of the digital images; classifying each of the detected and segmented morphologies and lesions into one or more identified categories for each of the digital images; assigning a global score to each of the digital images based on a count of the detected and segmented characteristic morphologies and lesions in each of the one or more identified categories;
(Continued)

analyzing the global scores of each of the digital images; and making an assessment of the clinical trial based on the analysis of the global scores of each of the digital images.

24 Claims, 4 Drawing Sheets

(51) Int. Cl.
    *G06T 7/11*         (2017.01)
    *G06T 7/90*         (2017.01)
    *G06T 7/70*         (2017.01)
    *G16H 30/20*       (2018.01)
    *G16H 10/20*       (2018.01)
    *A61B 5/00*         (2006.01)
    *G06K 9/62*         (2006.01)
    *G06N 3/08*         (2006.01)
    *G06T 7/40*         (2017.01)

(52) U.S. Cl.
CPC ............ *A61B 5/445* (2013.01); *A61B 5/4848* (2013.01); *A61B 5/7264* (2013.01); *G06K 9/628* (2013.01); *G06N 3/08* (2013.01); *G06T 7/11* (2017.01); *G06T 7/40* (2013.01); *G06T 7/70* (2017.01); *G06T 7/90* (2017.01); *G16H 10/20* (2018.01); *G16H 30/20* (2018.01); *G06T 2207/10024* (2013.01); *G06T 2207/20036* (2013.01); *G06T 2207/20064* (2013.01); *G06T 2207/20081* (2013.01); *G06T 2207/20084* (2013.01); *G06T 2207/30088* (2013.01); *G06T 2207/30096* (2013.01)

(56) References Cited

U.S. PATENT DOCUMENTS

| | | |
|---|---|---|
| 7,233,693 B2 | 6/2007 | Momma |
| 7,783,094 B2 | 8/2010 | Collins et al. |
| 8,000,777 B2 | 8/2011 | Jaeb |
| 8,194,952 B2 | 6/2012 | Mertz et al. |
| 8,260,010 B2 | 9/2012 | Chhibber et al. |
| 8,276,287 B2 | 10/2012 | Estocado |
| 8,505,209 B2 | 8/2013 | Estocado |
| 8,515,144 B2 | 8/2013 | Kuo |
| 8,588,893 B2 | 11/2013 | Jaeb |
| 9,089,303 B2 | 7/2015 | Chen et al. |
| 9,161,716 B2 | 10/2015 | Estocado |
| 9,990,472 B2 | 6/2018 | Gurcan et al. |
| 10,504,624 B2 | 12/2019 | Gurcan et al. |
| 2001/0049609 A1 | 12/2001 | Girouard et al. |
| 2004/0028263 A1 | 2/2004 | Sakamoto |
| 2004/0114800 A1 | 6/2004 | Ponomarev et al. |
| 2009/0196475 A1 | 8/2009 | Demirli et al. |
| 2010/0111387 A1 | 5/2010 | Christiansen |
| 2010/0284582 A1* | 11/2010 | Petit ........................ A61B 5/444 382/128 |
| 2013/0170718 A1 | 7/2013 | Ryu et al. |
| 2013/0179288 A1 | 7/2013 | Moses et al. |
| 2013/0331708 A1 | 12/2013 | Estocado |
| 2014/0036054 A1* | 2/2014 | Zouridakis ............ A61B 5/0077 348/77 |
| 2014/0095185 A1 | 4/2014 | Prior |
| 2014/0313303 A1 | 10/2014 | Davis et al. |
| 2015/0119721 A1 | 4/2015 | Pedersen |
| 2015/0150457 A1 | 6/2015 | Wu et al. |
| 2016/0157725 A1 | 6/2016 | Munoz |
| 2017/0039708 A1* | 2/2017 | Henry .................. A61B 5/4848 |
| 2017/0076446 A1 | 3/2017 | Pedersen et al. |
| 2017/0124709 A1* | 5/2017 | Rithe .................... G06K 9/2036 |
| 2017/0231550 A1* | 8/2017 | Do ........................ G06K 9/4652 382/128 |
| 2018/0028108 A1 | 2/2018 | Shluzas et al. |
| 2018/0235534 A1* | 8/2018 | Gareau .................. A61B 5/444 |

OTHER PUBLICATIONS

Chantharaphaichit, T. "Automatic Facial Acne Detection for Medical Treatment." Thesis submitted to Sirindhorn International Institute of Technology, Thammasat University. Oct. 2016. 61 pages.

Abas, et al., "Acne image analysis: lesion localization and classification," in SPIE Medical Imaging, 2016, pp. 97850B-97850B-9.

Azevedo-Marques et al., "Segmentation of dermatological ulcers using clustering of color components", CCECE 2013.

Burns et al., Development of a Wound Assessment System for Quantitative Chronic Wound Monitoring, p. 7-8, 2002.

Callieri et al., "Derma: monitoring the evolution of skin lesions with a 3D system", VMV 2003.

Casas et al., "Imaging technologies applied to chronic wounds", ISABEL '11, Oct. 26-29.

Contents:PictZar Basics, www.pictzar.com, Mar. 21, 2016.

Cukjati et al., Measures of wound healing rate, Proceedings of the 22nd Annual EMBS International Conference, Jul. 23-28, 2000, p. 765-768.

Dorileo et al., "Segmentation and analysis of the tissue composition of dermatological ulcers", CCECE 2010.

FAQ About PictZar Calibrated Digital Meazurements, www.pictzar.com, Mar. 21, 2016.

Fauzi, et al., "Computerized segmentation and measurement of chronic wound images," Comput Biol Med, vol. 60, pp. 74-85, May 1, 2015.

Filko et al., WIT A—Application for Wound Analysis and Management, 2010.

Hani et al., Haemoglobin Distribution in Ulcers for Healing Assessment, 2012 4th International Conference on Intelligent and Advanced Systems, 2011.

Hettiarachchi et al., Mobile Based Wound Measurement, p. 298-301, 2013.

Katapadi, et al., "Evolving strategies for the development and evaluation of a computerised melanoma image analysis system," Computer Methods in Biomechanics and Biomedical Engineering: Imaging & Visualization, pp. 1-8, 2017.

Kolesnik et al., Multi-dimensional Color Histograms for Segmentation of Wounds in Images p. 1014-1022, 2005.

Kolesnik et al., Segmentation of Wounds in the Combined Color-Texture Feature Space, Proc. of SPIE vol. 5370:549-556, 2004.

Loizou et al., Evaluation of Wound Healing Process Based on Texture Analysis, Proceedings of the 2012 IEEE 12th International Conference on Bioinformatics & Bioengineering (BIBE), Larnaca, Cyprus, Nov. 11-13, 2012.

Mukherjee et al., "Automated tissue classification framework for reproducible chronic wound assessment", Hindawi Publishing Corporation, BioMed Research International, vol. 2014, article ID 851582, 9 pages.

Oduncu et al., "Analysis of skin wound images using digital color image processing: a preliminary communication", Int. J. Low Extremity Wounds, vol. 3, No. 3, pp. 151-156, Sep. 2004.

Pereira et al., "Classification of dermatological ulcers based on tissue composition and color texture features", ISABEL 2011.

Perez et al., "Segmentation and Analysis of Leg Ulcers Color Images", p. 262-266, 2001.

PictZar Calibrated Digital Meazurements, www.pictzar.com, Mar. 21, 2016.

PictZar Tablet Interface Device Calibrated Digital Meazurements Samsung Windows 8 Tablet PC, www.pictzar.com, Mar. 21, 2016.

Song et al., Automated Wound Identification System Based on Image Segmentation and Artificial Neural Networks, 2012 IEEE International Conference on Bioinformatics and Biomedicine, p. 619-622, 2012.

Veredas et al., "Wound image evaluation with machine learning", Neurocomputing 164 (2015) 112-122, available online Mar. 14, 2015.

Veredas et al., "Binary Tissue Classification on Wound Images With Neural Networks and Bayesian Classifiers", IEEE Transactions on Medical Imaging vol. 29:410-427, 2010.

(56) References Cited

OTHER PUBLICATIONS

Wang et al., "Smartphone-based wound assessment system for patients with diabetes", IEEE Transactions on Biomedical Engineering, vol. 62, issue 2, Feb. 2015.

Wannous et al., "Enhanced assessment of the wound-healing process by accurate Multiview tissue classification", IEEE Transactions on Medical Imaging, vol. 30, issue 2, Feb. 2011.

Wannous et al., "Fusion of multi-view tissue classification based on wound 3D model", ACIVS 2008, LNCS vol. 5259.

Wannous et al., "Supervised Tissue Classification from Color Images for a Complete Wound Assessment Tool", Proceedings of the 29th Annual International Conference of the IEEE EMBS Cité Internationale, Lyon, France Aug. 23-26, 2007, p. 6031-6034.

Wantanajittikul et al., Automatic Segmentation and Degree Identification in Burn Color Images, The 2011 Biomedical Engineering International Conference, p. 169-173, 2011.

Weber et al., "Remote Wound Monitoring of Chronic Ulcers", IEEE Transactions on Information Technology in Biomedicine vol. 14:371-377, 2010.

International Preliminary Report on Patentability issued for Application No. PCT/US2018/054054, dated Apr. 16, 2020.

\* cited by examiner

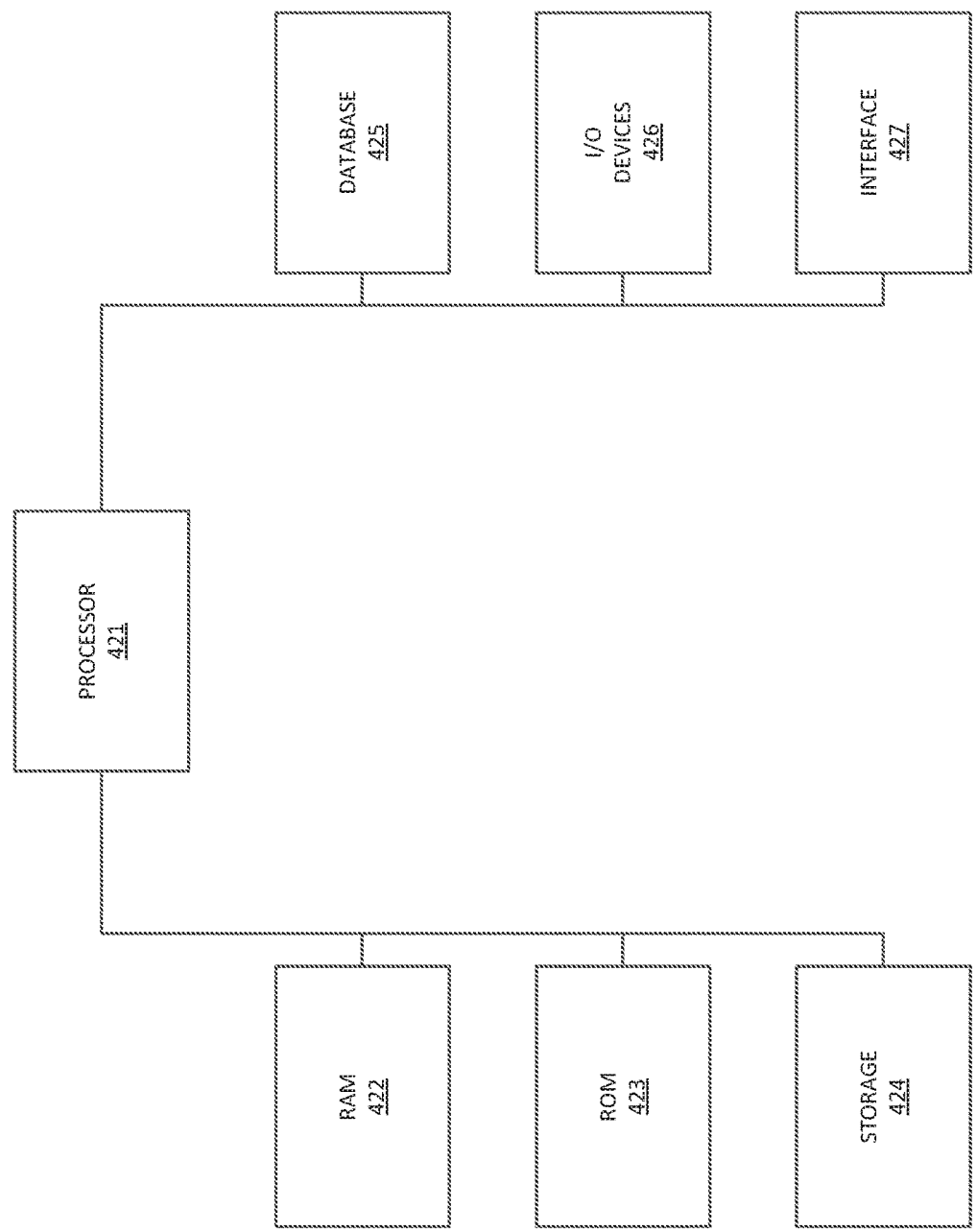

SYSTEM AND METHOD FOR IMAGE SEGMENTATION AND DIGITAL ANALYSIS FOR CLINICAL TRIAL SCORING IN SKIN DISEASE

CROSS-REFERENCE TO RELATED APPLICATION

This application is a national stage application filed under 35 U.S.C. § 371 of PCT/US2018/054054 filed Oct. 3, 2018, which claims priority to and benefit of U.S. provisional patent application Ser. No. 62/567,395 filed Oct. 3, 2017, which are fully incorporated by reference and made a part hereof.

BACKGROUND

Acne is a disease that affects around 85% of individuals during the course of life. Although it is typically seen in the teenage years, the adult form of acne may persist throughout adulthood in certain patients. Although the disease may be seen as inconsequential and a normal part of aging, in reality the disease has been shown to significantly deter the quality of life. Both suicide attempts and suicide are increased in the acne population. Costs are extensive with over $3 Billion in direct and indirect costs estimated each year attributed to acne in the US. Furthermore, in terms of life-altering affects, active acne and scarring residua may be associated with diminished job prospects throughout life.

There is no gold standard for acne evaluation in non-research clinics; it entirely depends on dermatologists' experience for acne severity evaluation. Counting lesions is the simplest and the most favored method of validating acne scoring for clinical trials. In acne diagnosis and treatment, it is important to accurately quantify or to evaluate the severity. Acne can be classified into several skin lesions including closed comedones (whiteheads), open comedones (blackheads), papules, pustules, cysts (nodules) and scars. It is difficult for a dermatologist to count and document each lesion type because of the limited time available during consultation. Furthermore, it is difficult to determine the efficacy of various treatment options as this requires repetitive visits by the patient to medical personnel over a period of time. Such visits can be time-consuming for the patient and the medical specialists, and efficacy of the treatment may be subject to subjectivity of medical personnel.

Determining the efficacy of clinical trials of treatments for other skin diseases such as rosacea also requires multiple visits to the dermatologists or other medical personnel and is subject to subjective determinations by the medical personnel on whether the skin disease is progressing, regressing or staying the same.

Therefore, systems and methods are desired that overcome challenges in the art, some of which are described above.

SUMMARY

Disclosed herein are computer-implemented systems and methods for clinical trial assessment of skin disease treatment. Digital images can be obtained and analyzed to validate the efficacy of clinical trials for treatment. Described herein are processes of region-of-interest determination using entropy-based filtering and thresholding as well as skin-disease lesion feature extraction. Feature extraction methods include using discrete wavelet frames and gray-level co-occurrence matrix in separating the skin disease into pre-identified lesion classes.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 4 illustrates an exemplary computer that can be used for image segmentation and digital analysis for clinical trial scoring in skin disease.

DETAILED DESCRIPTION

Figure 1:
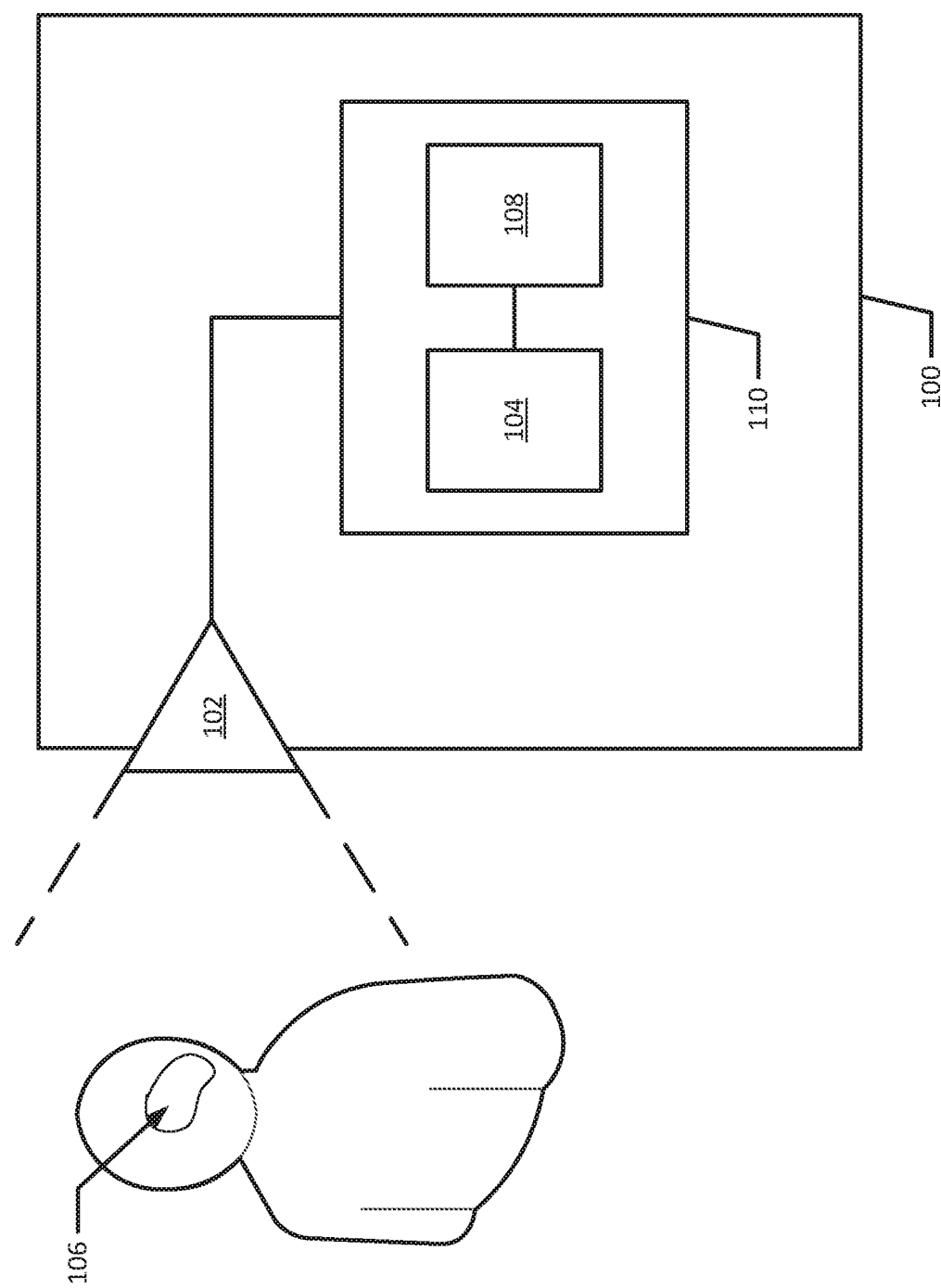
FIG. 1 illustrates an exemplary overview apparatus for image segmentation and digital analysis for clinical trial scoring in skin disease.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

FIG. 1 illustrates an exemplary overview apparatus for making clinical trial assessments of skin disease treatments. As shown in FIG. 1, one embodiment of the apparatus 100 comprises an image capture mechanism 102. In one aspect, the image capture mechanism 102 can be a camera. The image capture mechanism 102 can take still and/or video images. Generally, the image capture mechanism 102 will be a digital camera, but can be an analog device equipped with or in communication with an appropriate analog/digital converter. The image capture mechanism 102 may also be a webcam, scanner, recorder, or any other device capable of capturing a still image or a video.

As shown in FIG. 1A, the image capture mechanism 102 is in direct communication with a computing device 110 (e.g., computer) through, for example, a network (wired (including fiber optic)), wireless or a combination of wired and wireless) or a direct-connect cable (e.g., using a universal serial bus (USB) connection, IEEE 1394 "Firewire" connections, and the like). In other aspects, the image capture mechanism 102 can be located remotely from the computing device 110, but capable of capturing an image and storing it on a memory device such that the image can be downloaded or transferred to the computing device 110 using, for example, a portable memory device and the like. In one aspect, the computing device 110 and the image capture mechanism 102 can comprise or be a part of a device such as a smart device, smart phone, tablet, laptop computer or any other fixed or mobile computing device.

In a basic configuration, the computing device 110 can be comprised of a processor 104 and a memory 108. The processor 104 can execute computer-readable instructions that are stored in the memory 108. Moreover, images captured by the image capture device 102, whether still images or video, can be stored in the memory 108 and processed by the processor 104 using computer-readable instructions stored in the memory 108.

The processor 104 is in communication with the image capture device 102 and the memory 108. The processor 104 can execute computer-readable instructions stored on the memory 108 to capture, using the image capture device 102, an image. In one aspect, the captured image can include a series of digital images captured over a period of time of at least a portion of a subject, wherein each of the digital images includes an affected area 106 of a subject. The affected area 106 may be acne and/or rosacea.

The processor 104 can further execute computer-readable instructions stored on the memory 108 to capture, using the image capture device 102, a series of digital images over a period of time of the at least a portion of a subject, wherein each of the digital images includes the same affected area of the subject. The processor of the computer can execute computer-readable instructions to identify characteristic morphologies and lesions in the affected area of the subject in each of the digital images, wherein said identification comprises detection and segmentation of the characteristic morphologies and lesions in each of the digital images. The detected and segmented characteristic morphologies and lesions can be classified into one or more identified categories for each of the digital images.

In one example, detection may comprise the use of neural network algorithms. For example, detection and/or image classification may be performed using a convolutional neural network (CNN) such as "Inception V3," which can be trained using skin disease data (e.g., images of identified and classified skin diseases) such as acne and/or rosacea.

Figure 2:
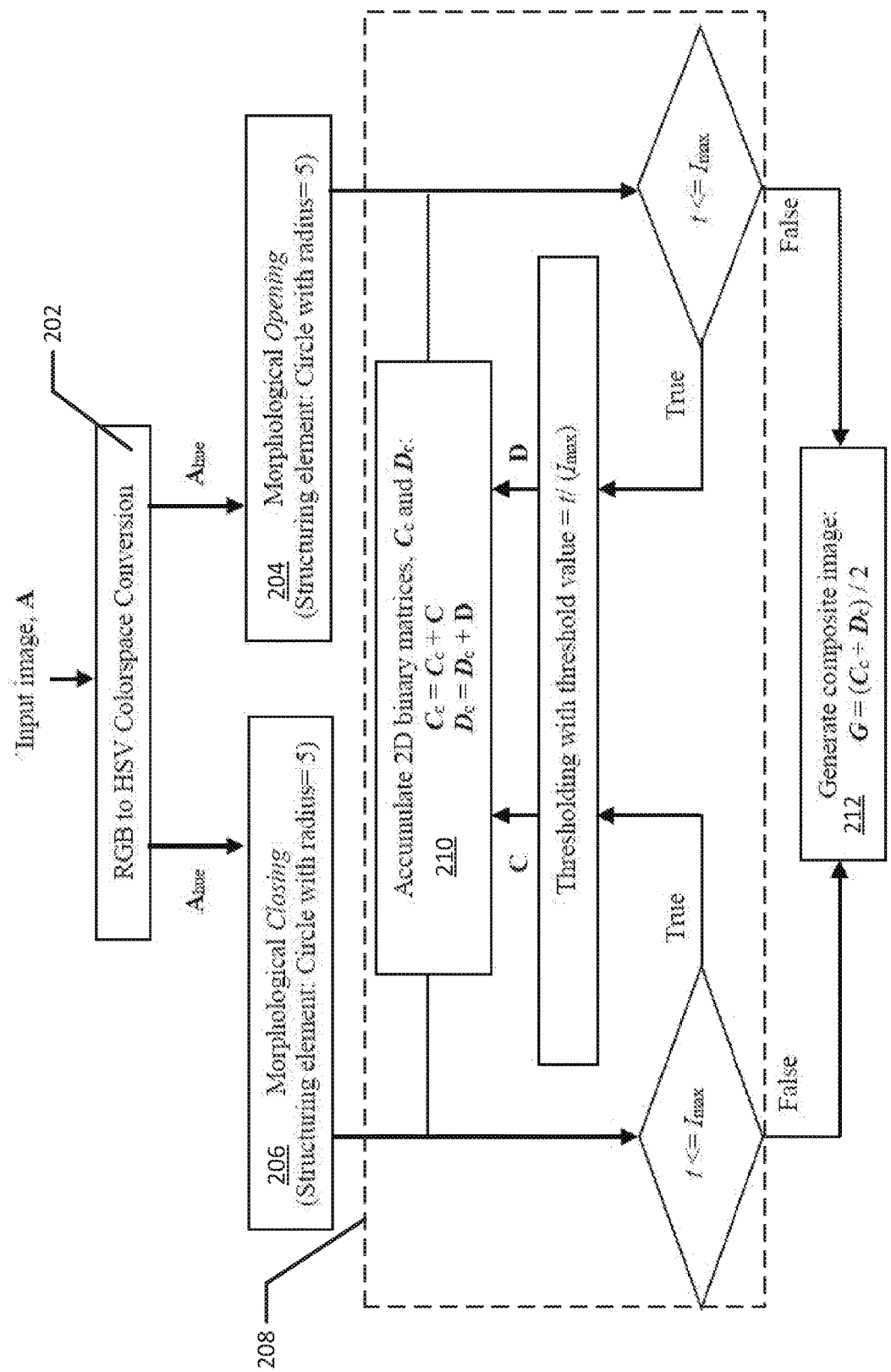
FIG. 2 is a flowchart illustrating the region-of-interest localization that generates the composite image showing regions-of-interest with regards to closed comedones and pustules types of acne lesion.

Consider another example where a region-of-interest is segmented particularly for closed comedones and pustules types of acne lesion, and the acne lesions are classified into six classes. Though this example focuses on acne, it can be applicable to other skin disease as well such as rosacea and the like. Acne lesion analysis is a challenging task because it has large inter-class variability within subjects and lesion types. From the perspective of region-of-interest extraction for digital image analysis, various approaches are needed to extract the meaningful acne affected areas. In this example, the regions-of-interests are extracted before individual lesions are detected. The typical appearance of the lesions and the surrounding skin areas in terms of color and textural characteristics is taken into consideration. FIG. 2 is a flowchart illustrating the region-of-interest localization that generates the composite image showing regions-of-interest with regards to closed comedones and pustules types of acne lesion.

The method disclosed relative to FIG. 2 involves 202, converting an input image into its equivalent Hue-Saturation-Value (HSV) color format representation. HSV separates color information from the luminance of an image; hence, by ignoring the saturation and the value components of the color space uneven illumination due to lighting variations on the image can be reduced and the color information utilized for further processing. The next steps perform morphological opening 204 and closing 206 on the hue component to enhance certain structural features from the image. An iterative thresholding approach 208 is performed on the images separately. For every iteration, an accumulator matrix 210 is generated that accumulates the binary 1 pixels from the outcome of each dichotomizing step. The number of iterations determines the resolution of the accumulation values. A composite image is then produced 212 by taking the average intensity values of the corresponding pixels of the closed image and the opened image.

The second part of the example demonstrates the feature extraction and supervised classification of acne lesions based on manually selected regions-of-interest. The feature bank is predominantly occupied by textural based features comprised of discrete wavelet frames (DWF) and gray-level co-occurrence matrix descriptors (GLCM).

Seemingly different from other wavelet-based approaches, DWF is invariant with respect to translations of the input signal. This property is quite desirable in the context of acne lesion classification. Channels are decomposed in DWF using a similar approach as the wavelet transform, but without the subsampling process resulting in four filtered images with the same size as the input image. The number of channels for DWF is similar as in the Pyramidal Wavelet Transform (PWT). As described herein, three levels of decomposition are performed. To compute the features, the mean energy E of each channel or filtered image is used and is given as:

$$E = \frac{1}{M \times N} \sum_{a=0}^{M-1} \sum_{b=0}^{N-1} |W_k(a, b)| \quad (1)$$

where M and N are the number of rows and columns of the channel or filtered images, and $W_k$ is the k-th channel of the filtered images.

Gray-level co-occurrence matrix (GLCM), also known as the gray-level spatial dependence matrix is a statistical method of examining texture that considers the spatial relationship of pixels. The GLCM functions characterize the texture of an image by calculating how often pairs of pixels with specific values and in a specified spatial relationship occur. Once a GLCM is created, statistical measures can be computed from the matrix.

GLCM is a statistical method that can well describe second-order statistics of a textured image. GLCM is a two-dimensional histogram in which each entry (i, j) corresponds to the number of occurrences of the pair of levels i and j which are a distance d apart. A co-occurrence matrix is specified by the relative frequencies P(i, j, d, θ) in which two pixels, separated by d, occur in a direction specified by the angle theta, one with gray level i and another with gray level j. GLCM is therefore a function of distance r and angle θ.

In the disclosed example, GLCM is computed for fixed d (=2) and θ=0°, 45°, 90° and 135°, which results in four GLCMs. Based on the GLCMs, the following features are calculated:

$$\text{Energy: } \sum_i \sum_j P^2(i, j) \quad (2)$$

$$\text{Maximum Probability: } \max_{i,j} P(i, j) \quad (3)$$

$$\text{Entropy: } -\sum_i \sum_j P(i, j) \log P(i, j) \quad (4)$$

$$\text{Dissimilarity: } \sum_i \sum_j |i - j| P(i, j) \quad (5)$$

$$\text{Contrast: } \sum_i \sum_j (i - j)^2 P^2(i, j) \quad (6)$$

$$\text{Inverse Difference Moment Normalized: } \sum_i \sum_j \frac{P^2(i, j)}{|i - j|}, i \neq j \quad (7)$$

$$\text{Correlation: } \sum_i \sum_j \frac{(i - \mu_x)(j - \mu_y) P(i, j)}{\sigma_x \sigma_y} \quad (8)$$

where $\mu_x$ and $\mu_y$ are the mean and standard deviation of $P_x$ and $P_y$, respectively.

In classifying the acne patterns, a fusion of features is used combining nine DWF features and eight GLCM-based features as described in Equation 2 to Equation 8, above. Using the methodology described in the example, classifying each of the detected and segmented characteristic morphologies and lesions into one or more identified categories for each of the digital images may comprise classifying each of the detected and segmented characteristic morphologies and lesions into one or more of open/closed comedones, pustules, papules, cysts, scars, and the like, or erythema (degree of redness), telangiectases or broken capillaries, plaques (raised plateau-like areas), and rhinophymatous changes (typically development of enlarged bumpy nose), and the like (which may be considered normal or abnormal morphologies).

Additional information about the results of the segmentation and classification example described above can be found in "Acne Image Analysis: Lesion Localization And Classification," Fazly Salleh Abas; Benjamin Kaffenberger; Joseph Bikowski; Metin N. Gurcan; Proceedings Volume 9785, Medical Imaging 2016: Computer-Aided Diagnosis; 97850B (2016); doi: 10.1117/12.2216444, presented at SPIE Medical Imaging, 2016, San Diego, Calif., United States, which is incorporated by reference and made a part hereof.

Once segmented and classified, the processor 104 can further execute computer-readable instructions stored on the memory 108 to assign, a global score to each of the digital images that comprise the series of digital images based on a count of the detected and segmented characteristic morphologies and lesions in each of the one or more identified categories.

The processor 104 further execute computer-readable instructions stored on the memory 108 to analyze the global scores of each of the digital images and make an assessment of the clinical trial based on the analysis of the global scores of each of the digital images.

Generally, the subject will be undergoing treatment for at least one skin disease over the period of time. This may involve medications such as those administered orally, through injection, topically, and the like, or any other form of treatment. The assessment of the clinical trial based on the analysis of the global scores of each of the digital images considers an efficacy of the treatment. For example, is the skin disease clearing (e.g., the affected area getting smaller), progressing (e.g., the affected area getting larger or new affected areas appearing), or staying the same during the period of time of the clinical trial.

Identifying characteristic morphologies and lesions in the affected area of the subject in each of the digital images where such identification comprises detection and segmentation of the characteristic morphologies and lesions in each of the digital images, may comprise the processor 104 identifying and registering a lesion in a latter of the series of digital images that was in an earlier of the series of digital images. Such registration enables determining a change in the lesion in the latter of the series of digital images that was in an earlier of the series of digital images. The change may comprise a change in one or more of size, shape, intensity or image characteristics of the lesion in the latter of the series of digital images that was in an earlier of the series of digital images. The processor 104 may determine if the change in one or more of size, shape, intensity or image characteristics of the lesion in the latter of the series of digital images that was in an earlier of the series of digital images is consistent with a normal disease progression with a sample medicine. For example, the computer may be pre-programmed with expected results for the sample medicine, and the actual results compared with the expected results, by the computer, to determine if the change in one or more of size, shape, intensity or image characteristics of the lesion in the latter of the series of digital images that was in an earlier of the series of digital images is consistent with a normal disease progression with a sample medicine. In one aspect, the processor 104 can be configured such that if the change in one or more of size, shape, intensity or image characteristics of the lesion in the latter of the series of digital images that was in an earlier of the series of digital images is not consistent with a normal disease progression with a sample medicine, then alerting a medical professional. For example, a display of the computer 100 can alert the medical professional by use of a dashboard displayed on a screen of the computer 100 or another electronic device such as a smart phone or other portable electronic device.

In some aspects, the memory 108 may be used to store an electronic database comprising the series of images and information about any identified characteristic morphologies and lesions in the affected area of the subject in each of the digital images. The information about any identified characteristic morphologies and lesions in the affected area of the subject in each of the digital images may include a size of the identified characteristic morphologies and lesions in the affected area of the subject in each of the digital images.

As noted herein, the image capture device 102 does not have to be a part of or affixed to the computer 100. For example, at least one image of the series of images can be captured in electronic format by the subject and transmitted to the computer 100. This form of image capture and transmittal may alleviate the need for the subject to travel to a location where the medical professional is located. Such convenience may increase the subject's participation in the clinical trial. For example, the subject may capture the at least one image of the series of images using a camera of the subject's smartphone and then transmit the captured image or images to the computer 100 via a text message or by email.

Figure 3:
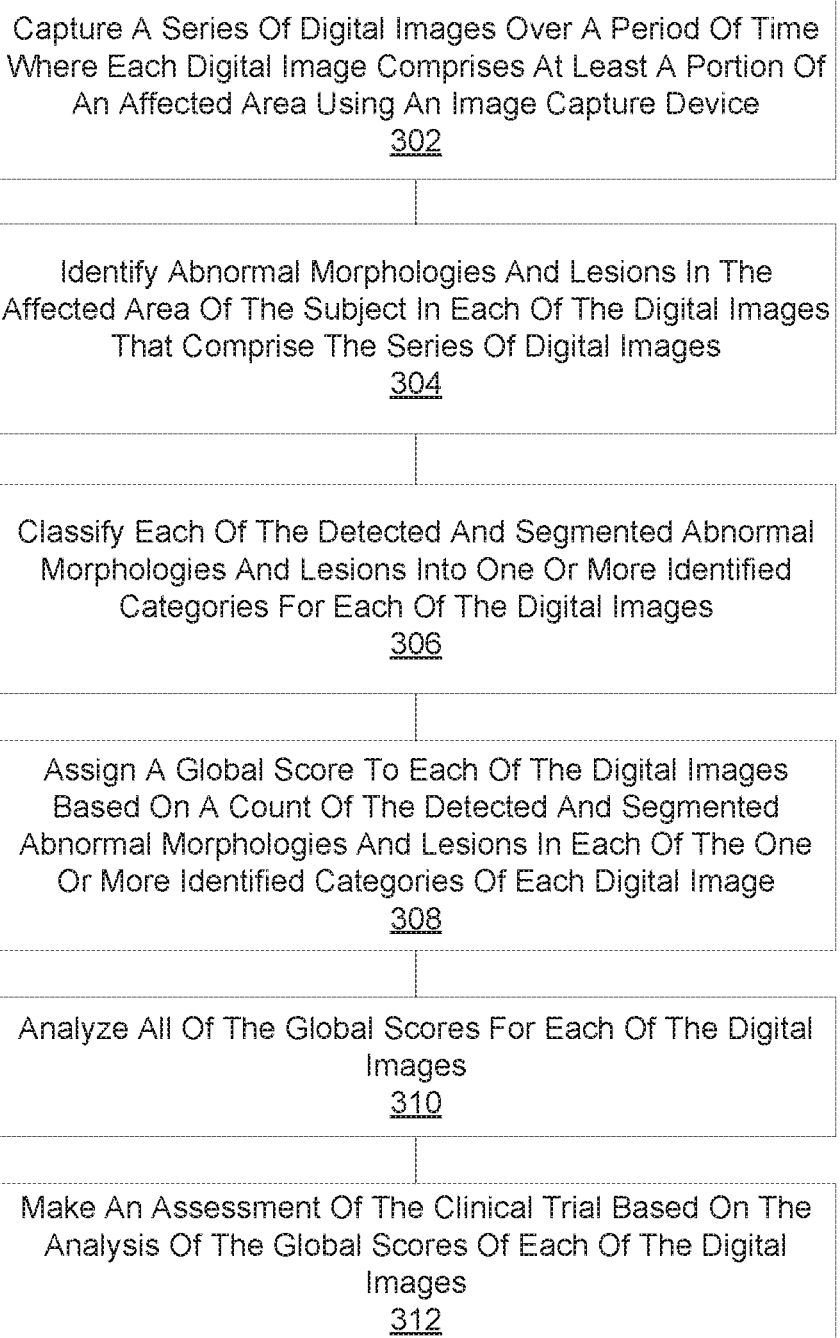
FIG. 3 is a flowchart that illustrates an exemplary method of image segmentation and digital analysis for clinical trial scoring in skin disease.

The system and methods described above and illustrated with reference to FIGS. 1 and 2 may also benefit from adaptive learning. For example, feedback can be provided by experts that evaluation the segmentation of the images and the segmentation and classification parameters can be updated based on the positive and negative feedback FIG. 3 is a flowchart that illustrates an exemplary method for clinical trial assessment of skin disease treatment comprising 302, obtaining a series of digital images over a period of time, wherein at least a portion of each of the digital images comprise an affected area (i.e., exhibiting indications of a skin disease). The digital images may be obtained directly via an image capture device as described herein, retrieved from a file, and the like. For example, a subject could be prompted to take a picture of his or her affected area and email, text or otherwise transmit it to their medical professional for analysis. This could occur on a periodic basis. The period of time can be, for example, a week, a month, two months, three months, a year, two years, etc., as such period of time is defined by the medical professional conducting the clinical trial.

At 304, characteristic morphologies and lesions in the affected area of the subject in each of the digital images are identified. Such identification comprises detection and segmentation of the characteristic morphologies and lesions in each of the digital images.

In one aspect, segmentation of the characteristic morphologies and lesions in each of the digital images comprises performing color space normalization on each of the series of digital images to determine one or more hue components for each digital image of the series of digital images; performing morphological opening and closing on the one or more hue components to enhance structural features for each digital image of the series of digital images and to create a morphological opening image and a morphological closing image for each digital image of the series of digital images; performing iterative thresholding on each of the morphological opening image and the morphological closing image for each digital image of the series of digital images; producing a composite image for each digital image of the series of digital images by taking an average between the morphological opening image and the morphological closing image for each digital image of the series of digital images.

At 306, each of the detected and segmented characteristic morphologies and lesions are classified into one or more identified categories for each of the digital images. For example, classifying each of the detected and segmented characteristic morphologies and lesions into one or more identified categories for each of the digital images may comprise classifying each of the detected and segmented characteristic morphologies and lesions into one or more of open/closed comedones, pustules, papules, cysts, scars, erythema (degree of redness), telangiectases or broken capillaries, plaques (raised plateau-like areas), and rhinophymatous changes (typically development of enlarged bumpy nose), and the like. This can be performed by determining a plurality of textural based features of each composite image and classifying each of the detected and segmented characteristic morphologies and lesions into the one or more identified categories based on the determined textural based features. The determined textural based features may comprise one or more discrete wavelet frames (DWF) and one or more gray-level co-occurrence matrix descriptors (GLCM). For example, the determined textural based features may comprise nine DWF features and eight GLCM features.

At 308, a global score is assigned to each of the digital images based on a count of the detected and segmented characteristic morphologies and lesions in each of the one or more identified categories. At 310, the global scores for each of the series of digital images are analyzed to make, at 312, an assessment of the clinical trial based on the analysis of the global scores of each of the digital images. Such an assessment may comprise, for example, determining that the clinical trial is successful (e.g., the affected area has been eliminated or reduce by a desired amount), unsuccessful (e.g., the affected area has not reduced in size and/or intensity, new affected areas have developed, etc.), additional testing/trials are needed, and the like.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for discriminating tissue of a specimen. In one exemplary aspect, the units can comprise a computing device that comprises a processor 321 as illustrated in FIG. 4 and described below.

FIG. 4 illustrates an exemplary computer that can be used for clinical trial assessment of skin disease treatment. As used herein, "computer" may include a plurality of computers. The computers may include one or more hardware components such as, for example, a processor 421, a random access memory (RAM) module 422, a read-only memory (ROM) module 423, a storage 424, a database 425, one or more input/output (I/O) devices 426, and an interface 427. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 424 may include a software partition associated with one or more other hardware components. It is understood that the components listed above are exemplary only and not intended to be limiting.

Processor 421 may include one or more processors, each configured to execute instructions and process data to perform one or more functions associated with a computer for making a clinical trial assessment of skin disease treatment. Processor 421 may be communicatively coupled to RAM 422, ROM 423, storage 424, database 425, I/O devices 426, and interface 427. Processor 421 may be configured to execute sequences of computer program instructions to perform various processes. The computer program instructions may be loaded into RAM 422 for execution by processor 421.

RAM 422 and ROM 423 may each include one or more devices for storing information associated with operation of processor 421. For example, ROM 423 may include a memory device configured to access and store information associated with the computer, including information for identifying, initializing, and monitoring the operation of one or more components and subsystems. RAM 422 may include a memory device for storing data associated with one or more operations of processor 421. For example, ROM 423 may load instructions into RAM 422 for execution by processor 421.

Storage 424 may include any type of mass storage device configured to store information that processor 421 may need to perform processes consistent with the disclosed embodiments. For example, storage 424 may include one or more magnetic and/or optical disk devices, such as hard drives, CD-ROMs, DVD-ROMs, or any other type of mass media device.

Database 425 may include one or more software and/or hardware components that cooperate to store, organize, sort, filter, and/or arrange data used by the computer and/or processor 421. For example, database 425 may store digital images of an affected area, computer-executable instructions for identifying characteristic morphologies and lesions in the affected area of the subject in each of the digital images; classifying the characteristic morphologies and lesions in the affected area of the subject in each of the digital images; assigning a global score to each of the digital images based on a count of the detected and segmented characteristic morphologies and lesions in each of the one or more identified categories of each digital image; analyzing the global scores of each of the digital images that comprise the series of digital images; and making an assessment of the clinical trial based on the analysis of the global scores of each of the digital. It is contemplated that database 325 may store additional and/or different information than that listed above.

I/O devices 426 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 426 may also include a display including a graphical user interface (GUI) for outputting information on a monitor. I/O devices 426 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, a camera, or any other suitable type of interface device.

Interface 427 may include one or more components configured to transmit and receive data via a communication network, such as the Internet, a local area network, a workstation peer-to-peer network, a direct link network, a wireless network, or any other suitable communication platform. For example, interface 427 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computer-implemented method for assessment of a skin disease comprising:
    obtaining, by a computer, a series of digital images over a period of time of at least a portion of a subject, wherein each of the digital images includes an affected area of the subject;
    identifying, by the computer, characteristic morphologies and lesions in the affected area of the subject in each of the digital images, wherein said identification comprises detection and segmentation of the characteristic morphologies and lesions in each of the digital images;
    classifying, by the computer, each of the detected and segmented characteristic morphologies and lesions into one or more identified categories for each of the digital images;
    assigning, by the computer, a global score to each of the digital images based on a count of the detected and segmented characteristic morphologies and lesions in each of the one or more identified categories;
    analyzing, by the computer, the global scores of each of the digital images; and
    making, by the computer, an assessment based on the analysis of the global scores of each of the digital images,
    wherein segmentation of the characteristic morphologies and lesions in each of the digital images comprises:
        performing color space normalization on each of the series of digital images to determine one or more hue components for each digital image of the series of digital images;
        performing morphological opening and closing on the one or more hue components to enhance structural features for each digital image of the series of digital images and to create a morphological opening image and a morphological closing image for each digital image of the series of digital images;
        performing iterative thresholding on each of the morphological opening image and the morphological closing image for each digital image of the series of digital images; and
        producing a composite image for each digital image of the series of digital images by taking an average of intensity values of corresponding pixels of the morphological opening image and the morphological closing image for each digital image of the series of digital images.

2. The method of claim 1, further comprising performing color space normalization on each of the series of digital images.

3. The method of claim 2, wherein performing color space normalization on each of the series of digital images comprises converting each of the digital images into its hue-saturation-value (HSV) color format representation.

4. The method of claim 1, wherein performing color space normalization on each of the series of digital images comprises converting each of the digital images into its hue-saturation-value (HSV) color format representation.

5. The method of claim 1, wherein classifying, by the computer, each of the detected and segmented characteristic morphologies and lesions into one or more identified categories for each of the digital images comprises determining a plurality of textural based features of each composite image and classifying each of the detected and segmented characteristic morphologies and lesions into the one or more identified categories based on the determined textural based features.

6. The method of claim 5, wherein the determined textural based features comprise one or more discrete wavelet frames (DWF) and one or more gray-level co-occurrence matrix descriptors (GLCM).

7. The method of claim 6, wherein the determined textural based features comprise nine DWF features and eight GLCM features.

8. A computer-implemented method for assessment of temporal changes of a skin disease of a subject comprising:
    obtaining a first digital image at a first time, wherein at least a portion of the first digital image comprises an affected area of the subject;
    identifying, by a computer, characteristic morphologies and lesions in the affected area of the subject in the first digital image, wherein said identification comprises detection and segmentation of the characteristic morphologies and lesions in the first digital image;
    classifying, by the computer, each of the detected and segmented characteristic morphologies and lesions into one or more identified categories for the first digital image;
    assigning, by the computer, a global score to the first digital image based on a count of the detected and segmented characteristic morphologies and lesions in each of the one or more identified categories;
    obtaining a second digital image of the at least the portion of the affected area, wherein the second digital image is captured at a second time that is after the first digital image was captured;
    identifying, by a computer, characteristic morphologies and lesions in the affected area of the subject in the second digital image, wherein said identification comprises detection and segmentation of the characteristic morphologies and lesions in the second digital image;

classifying, by the computer, each of the detected and segmented characteristic morphologies and lesions into one or more identified categories for the second digital image;

assigning, by the computer, a global score to the second digital image based on a count of the detected and segmented characteristic morphologies and lesions in each of the one or more identified categories;

analyzing, by the computer, the global scores of each of the first and second digital images; and making, by the computer, an assessment based on the analysis of the global scores of each of the first and second digital images, wherein segmentation of the characteristic morphologies and lesions in each of the first and second digital images comprises:

performing color space normalization on each of the first and second digital images to determine one or more hue components for each of the first and second digital images;

performing morphological opening and closing on the one or more hue components to enhance structural features for each of the first and second digital images and to create a morphological opening image and a morphological closing image for each of the first and second digital images;

performing iterative thresholding on each of the morphological opening image and the morphological closing image for each of the first and second digital images; and producing a composite image for each of the first and second digital images by taking an average of intensity values of corresponding pixels of the morphological opening image and the morphological closing image for each of the first and second digital images.

9. The method of claim 8, further comprising performing color space normalization on each of the first and second digital images.

10. The method of claim 9, wherein performing color space normalization on each of the first and second digital images comprises converting each of the digital images into its hue-saturation-value (HSV) color format representation.

11. The method of claim 8, wherein performing color space normalization on each of the first and second digital images comprises converting each of the first and second digital images into its hue-saturation-value (HSV) color format representation.

12. The method of claim 8, wherein classifying, by the computer, each of the detected and segmented characteristic morphologies and lesions into one or more identified categories for each of the first and second digital images comprises determining a plurality of textural based features of each composite image and classifying each of the detected and segmented characteristic morphologies and lesions into the one or more identified categories based on the determined textural based features.

13. The method of claim 12, wherein the determined textural based features comprise one or more discrete wavelet frames (DWF) and one or more gray-level co-occurrence matrix descriptors (GLCM).

14. The method of claim 13, wherein the determined textural based features comprise nine DWF features and eight GLCM features.

15. A system for assessment of a skin disease comprising:
an image capture device; and
a computer comprising a processor in communication with a memory, wherein the processor executes computer-readable instructions stored in the memory that cause the processor to;

obtain, from the image capture device, a series of digital images over a period of time of at least a portion of a subject, wherein each of the digital images includes an affected area of the subject;

identify characteristic morphologies and lesions in the affected area of the subject in each of the digital images, wherein said identification comprises detection and segmentation of the characteristic morphologies and lesions in each of the digital images;

classify each of the detected and segmented characteristic morphologies and lesions into one or more identified categories for each of the digital images;

assign a global score to each of the digital images based on a count of the detected and segmented characteristic morphologies and lesions in each of the one or more identified categories;

analyze the global scores of each of the digital images; and make an assessment based on the analysis of the global scores of each of the digital images, wherein the processor executing computer-readable instructions stored in the memory for segmentation of the characteristic morphologies and lesions in each of the digital images comprises the processor executing computer-readable instructions stored in the memory to:

perform color space normalization on each of the series of digital images to determine one or more hue components for each digital image of the series of digital images;

perform morphological opening and closing on the one or more hue components to enhance structural features for each digital image of the series of digital images and to create a morphological opening image and a morphological closing image for each digital image of the series of digital images;

perform iterative thresholding on each of the morphological opening image and the morphological closing image for each digital image of the series of digital images; and produce a composite image for each digital image of the series of digital images by taking an average of intensity values of corresponding pixels of the morphological opening image and the morphological closing image for each digital image of the series of digital images.

16. The system of claim 15, further comprising the processor executing computer-readable instructions stored in the memory to perform color space normalization on each of the series of digital images.

17. The system of claim 16, wherein performing color space normalization on each of the series of digital images comprises the processor executing computer-readable instructions stored in the memory to convert each of the digital images into its hue-saturation-value (HSV) color format representation.

18. The system of claim 15, wherein performing color space normalization on each of the series of digital images comprises the processor executing computer-readable instructions stored in the memory to convert each of the digital images into its hue-saturation-value (HSV) color format representation.

19. The system of claim 15, wherein classifying each of the detected and segmented characteristic morphologies and lesions into one or more identified categories for each of the digital images comprises the processor executing computer-readable instructions stored in the memory to determine a plurality of textural based features of each composite image and classifying each of the detected and segmented characteristic morphologies and lesions into the one or more identified categories based on the determined textural based features.

20. The system of claim 19, wherein the determined textural based features comprise one or more discrete wavelet frames (DWF) and one or more gray-level co-occurrence matrix descriptors (GLCM).

21. The system of claim 20, wherein the determined textural based features comprise nine DWF features and eight GLCM features.

22. The method of claim 1, wherein the assessment is an assessment of a clinical trial of a treatment for the skin disease.

23. The computer-implemented method of claim 8, wherein the assessment is an assessment of a clinical trial of a treatment for the skin disease.

24. The system of claim 15, wherein the assessment is an assessment of a clinical trial of a treatment for the skin disease.

\* \* \* \* \*